(12) United States Patent
Ji (10) Patent No.: US 10,994,905 B2
(45) Date of Patent: May 4, 2021

(54) PACKING BOX AND METHOD FOR USING THE SAME

(71) Applicant: GUANGZHOU OO MEDICAL SCIENTIFIC LIMITED, Guangzhou (CN)

(72) Inventor: Li Ji, Guangzhou (CN)

(73) Assignee: GUANGZHOU OO MEDICAL SCIENTIFIC LIMITED, Guangzhou (CN)

( * ) Notice: Subject to any disclaimer, the term of this patent is extended or adjusted under 35 U.S.C. 154(b) by 518 days.

(21) Appl. No.: 15/798,399

(22) Filed: Oct. 31, 2017

(65) Prior Publication Data

US 2018/0339821 A1 Nov. 29, 2018

(30) Foreign Application Priority Data

May 23, 2017 (CN) .......................... 201710369795.7

(51) Int. Cl.
*A61C 19/02* (2006.01)
*A61C 7/14* (2006.01)
(Continued)

(52) U.S. Cl.
CPC .............. *B65D 51/249* (2013.01); *A61C 7/14* (2013.01); *B65D 43/14* (2013.01); *A61B 50/20* (2016.02);
(Continued)

(58) Field of Classification Search
CPC ......... A61B 50/22; A61B 50/24; A61B 50/20; A61B 50/30; A61B 50/33; A61C 19/00;
(Continued)

(56) References Cited

U.S. PATENT DOCUMENTS 860,648 A * 7/1907 Feldman ................ B65D 43/24
40/313
883,906 A * 4/1908 Swan ........................ A47F 3/00
312/123

(Continued)

FOREIGN PATENT DOCUMENTS

CN 2442564 Y 8/2001
CN 202292724 U 7/2012
(Continued)

OTHER PUBLICATIONS

CN First Office Action dated Jan. 31, 2018, in the corresponding CN application (application No. 201710369795.7).
(Continued)

*Primary Examiner* — Gideon R Weinerth
(74) *Attorney, Agent, or Firm* — Lathrop GPM LLP (57) ABSTRACT

The present disclosure discloses a packing box and a method for using the same. The packing box includes a box body and a cover; the cover matches the box body, and an end of the cover is connected on a swivel to an end of the box body; an inner side of the cover is provided with an non-slip layer; the lower end surface is flush with a lower end of the cover or protrudes with respect to the lower end of the cover; after the cover is turned over, a bottom support surface is formed. The method of using a packing box includes: opening the packing box, turning over a cover, and placing the packing box after the cover being turned over on a working surface. The packing box of the present disclosure has an non-slip function; the box and the method disclosed bring convenience for people to use the box.

15 Claims, 10 Drawing Sheets

(51) Int. Cl.
*B65D 43/14* (2006.01)
*B65D 51/24* (2006.01)
*A61B 50/20* (2016.01)
*B65D 5/52* (2006.01)

(52) U.S. Cl.
CPC .............. *A61C 7/146* (2013.01); *A61C 19/02* (2013.01); *A61C 2202/00* (2013.01); *B65D 5/5206* (2013.01)

(58) Field of Classification Search
CPC ........... A61C 7/14; A61C 7/146; A61C 8/009; A61C 2202/00; A61C 2202/01; A61C 2202/02; A61C 19/02; A61G 15/14; A61G 15/16; B65D 25/10; B65D 25/107; B65D 43/14; B65D 43/24; B65D 5/5206; B65D 51/249; B65D 43/02; E05D 3/00; E05D 2005/108; E05D 2005/145; E05D 2011/1092; E05D 11/1028; E05D 11/1078
USPC ....... 292/262, 266, 270, 272, 274, 297, 305; 16/DIG. 33, 287, 311, 319, 366, 370, 371, 16/321, 337; 220/845, 502, 23.87, 817; 433/77, 79; 206/45.23, 63.5; 248/354.5, 248/354.6; 217/60 R, 60 B, 60 C
See application file for complete search history.

(56) References Cited

U.S. PATENT DOCUMENTS

| | | | | | |
|---|---|---|---|---|---|
| 1,203,659 | A | * | 11/1916 | Smith | A47B 23/043 248/456 |
| 1,653,696 | A | * | 12/1927 | Clayton | B65D 43/24 40/313 |
| 1,920,466 | A | * | 8/1933 | Haskins | E05D 3/02 16/386 |
| 1,951,408 | A | * | 3/1934 | Haven | B65D 5/5206 206/425 |
| 2,014,176 | A | * | 9/1935 | Henderson | A47B 23/043 248/456 |
| 2,018,271 | A | * | 10/1935 | Lewis | A24F 19/00 220/632 |
| 3,288,500 | A | * | 11/1966 | Hamel | B60G 7/02 403/228 |
| 3,833,098 | A | * | 9/1974 | Alderman | A45C 9/00 190/11 |
| 4,099,647 | A | | 7/1978 | Bergh et al. | |
| 5,482,067 | A | * | 1/1996 | Wittrock | A61C 19/02 134/115 R |
| 5,823,773 | A | * | 10/1998 | Brysch | A61C 19/00 433/77 |
| 6,305,652 | B1 | * | 10/2001 | Borke | A47B 23/002 248/174 |
| 6,450,328 | B1 | * | 9/2002 | Machacek | A61C 19/02 206/45.2 |
| 6,543,949 | B1 | * | 4/2003 | Ritchey | A47B 21/0314 400/691 |
| 6,740,355 | B2 | * | 5/2004 | Thiemann | A01K 5/0114 427/180 |
| 7,207,540 | B2 | * | 4/2007 | Thomas | F16M 13/00 248/346.01 |
| 7,753,203 | B2 | * | 7/2010 | Lampropoulos | A61M 5/008 206/366 |
| 7,784,638 | B2 | * | 8/2010 | Kishbaugh | A47J 36/04 220/573.3 |
| 8,540,202 | B2 | * | 9/2013 | Hu | F16M 11/10 248/371 |
| 2007/0138042 | A1 | * | 6/2007 | Wood | A61C 3/04 206/369 |
| 2008/0166682 | A1 | * | 7/2008 | Bjorn | A61B 50/20 433/77 |
| 2010/0051491 | A1 | * | 3/2010 | Lampropoulos | A61B 50/20 206/366 |
| 2010/0146734 | A1 | * | 6/2010 | Munson | E05D 5/121 16/334 |
| 2010/0276560 | A1 | * | 11/2010 | Farris-Gilbert | F16M 11/10 248/346.3 |
| 2013/0001393 | A1 | * | 1/2013 | Hu | F16M 11/38 248/371 |
| 2013/0104341 | A1 | * | 5/2013 | Kenerly | E05D 3/02 16/273 |
| 2013/0181106 | A1 | * | 7/2013 | Lin | F16M 13/00 248/463 |
| 2013/0194741 | A1 | * | 8/2013 | Uchiyama | G06F 1/1681 361/679.26 |
| 2014/0059805 | A1 | * | 3/2014 | Krahn | G06F 1/1681 16/342 |
| 2014/0311927 | A1 | * | 10/2014 | Kang | B65D 5/5206 206/45.28 |
| 2015/0309539 | A1 | * | 10/2015 | Kamphuis | G06F 1/1616 361/679.27 |
| 2016/0030617 | A1 | * | 2/2016 | Hawkes | A61L 2/26 206/438 |
| 2018/0338823 | A1 | * | 11/2018 | Ji | A61C 19/02 |
| 2018/0339821 | A1 | * | 11/2018 | Ji | A61C 7/14 |
| 2020/0078141 | A1 | * | 3/2020 | Ji | A61C 7/287 |
| 2020/0288861 | A1 | * | 9/2020 | Chang | A47B 23/043 |

FOREIGN PATENT DOCUMENTS

| | | |
|---|---|---|
| CN | 202987714 U | 6/2013 |
| CN | 203283689 U | 11/2013 |
| CN | 204110528 U | 1/2015 |
| CN | 204124518 U | 1/2015 |
| CN | 205221335 U | 5/2016 |
| CN | 206857262 U | 1/2018 |
| JP | 2005168433 A | 6/2005 |
| KR | 20100004404 U | 4/2010 |

OTHER PUBLICATIONS

CN Second Office Action dated 2018, in the corresponding CN application (application No. 201710369795.7).
CN First Search Report dated Mar. 22, 2018 in the corresponding CN application(application No. 201710369795.7).
CN Second Search Report in the corresponding CN application(application No. 201710369795.7).

* cited by examiner

PACKING BOX AND METHOD FOR USING THE SAME

CROSS REFERENCE TO RELATED APPLICATIONS

The present application claims the priority of Chinese Patent Application No. 201710369795.7, filed May 23, 2017, the entire disclosures of which are incorporated herein by reference.

FIELD

The present disclosure relates to the technical field of packing articles, and more particularly, to a packing box and method for using the same.

BACKGROUND

A packing box is a box used to pack a product; it can guarantee the safety of the product in transit, upgrade the product, and so on.

There are a wide variety of existing packing boxes, one of which mainly comprises a box body and cover, the cover being connected on a swivel to box body. However, most of these packing boxes do not have an non-slip function. When such box is placed on a surface, since it has no non-slip setting, such box is easy to drop, knock over, and so on because of someone's carelessness, so that the product in the box is dropped, lost or destroyed, which brings inconvenience for people using the packing box and cannot protect the product better.

For example, regarding to the packing box for a bracket, if a bracket packing box placed on a surface is dropped, knocked over, and so on, the bracket in the bracket packing box will drop, or even lost, thus affecting the orthodontia by a doctor.

SUMMARY

It is an object of the present disclosure to provide a packing box and a method of using the same, which make it easy for people to use the packing box so as to protect the product in the packing box better.

A technical solution is as follows:

a packing box comprises a box body and a cover, the cover fits the box body, and an end of the cover is connected on a swivel to an end of the box body;

an inner side of the cover is provided with an non-slip layer, and the non-slip layer has a lower end surface being flush with a lower end of the cover or protruding with respect to the lower end of the cover;

after the cover is turned over, the lower end of the cover and the lower end surface of the non-slip layer form a bottom support surface, or after the cover is turned over, the lower end surface of the non-slip layer forms a bottom support surface.

Furthermore, the lower end surface of the non-slip layer may be adhered or adsorbed on a working surface.

Furthermore, an end of the cover and the box body is provided with a rotation block, the rotation block has a first rotation portion and a second rotation portion and is provided with at least two shaft holes; the shaft holes include at least a first shaft hole provided in the first rotation portion and a second shaft hole provided in the second rotation portion;

the first shaft hole is provided with a first rotation shaft connected to an end of the cover, and the second shaft hole is provided with a second rotation shaft connected to an end of the box body;

the cover is 360-degree connected on a swivel to the box body.

Furthermore, the first shaft hole and the second shaft hole are respectively provided with an elastic member, and the elastic member allows the cover to hold at any turning angle; the elastic member in the first shaft hole is connected to the first rotation shaft, and the elastic member in the second shaft hole is connected to the second rotation shaft.

Furthermore, the elastic member is a C-shaped elastic column.

Furthermore, an end of the cover and box body is respectively provided with a protruding portion, and the protruding portion forms a mounting recess on both sides of an end of the cover and box body respectively and is provided with a connection hole;

the rotation block is provided at the mounting recess of the cover and the box body, the first rotation shaft is connected to the connection hole of the protruding portion of the cover, and the second rotation shaft is connected to the connecting hole of the protruding portion of the box body.

Furthermore, at least one of two sides of the cover is provided with a fixing protrusion, a position limiting protrusion, and a support member; the fixing protrusion is distanced from the position limiting protrusion and is provided with a locking convex at an end, the support member is provided with a rotation hole and a position limiting slot and is connected on a swivel to the fixing protrusion though the rotation hole, and the position limiting slot fits the position limiting protrusion;

at least one of two sides of the box body is provided with a position determining protrusion, and the position determining protrusion corresponds to the position limiting protrusion and fits the position limiting slot.

Furthermore, the support member is further provided with a position determining slot; the position determining slot fits the position determining protrusion, is provided between the rotation hole and the position limiting slot of the support member, and has an orientation that is the same as or opposite to the orientation of the position limiting slot.

Furthermore, it further comprises an inner holder, and the box body is provided with a placing cavity; the inner holder is disposed in the placing cavity of the box body and is provided with a plurality of bracket-placing grooves; the inner holder has an upper surface, and a gap is left between the lower end surface of the non-slip layer and the upper surface of the inner holder when the packing box is closed.

Furthermore, the bracket-placing groove has a placement mouth, a placement side portion and a placement bottom portion, and a corresponding placing mark is set on at least one of a surface of the inner holder close to the placement mouth of the bracket-placing groove, the placement side portion of the bracket-placing groove and the placement bottom portion of the bracket-placing groove.

Furthermore, the upper surface of the inner holder is protruded upwardly to form a boss, and a plurality of bracket-placing grooves are provided on the boss; the non-slip layer is provided with a through hole corresponding to the boss; and the inner side of the cover is provided with a flange corresponding to the boss, and the flange and an inner end portion of the cover form the placing groove corresponding to the non-slip layer; the non-slip layer is provided in the placing groove of the cover.

Furthermore, the boss has a first edge and a second edge, and the bracket-placing grooves are divided into first bracket-placing grooves, second bracket-placing grooves and third bracket-placing grooves; the first bracket-placing grooves are disposed adjacent to the first edge and regularly arranged along the first edge, the second bracket-placing grooves are disposed adjacent to the second edge and regularly arranged along the second edge, and the first bracket-placing grooves correspond to the second bracket-placing grooves; the third bracket-placing grooves are regularly arranged between the first bracket-placing grooves and the second bracket-placing grooves.

Furthermore, the boss is in a shape of an ellipse, the first bracket-placing grooves are disposed adjacent to the first edge and arranged in an arc along the first edge, and the second bracket-placing grooves are disposed adjacent to the second edge and arranged in an arc along the second edge.

Furthermore, there are twenty-eight bracket-placing grooves, consisting of ten first bracket-placing grooves, ten second bracket-placing grooves and eight third bracket-placing grooves.

Furthermore, among the ten first bracket-placing grooves regularly arranged, the third of the first bracket-placing grooves and the eighth of the first bracket-placing grooves are respectively provided with a traction hook avoiding groove; the traction hook avoiding groove is communicated with the first bracket-placing groove and protrudes outwardly with respect to the first bracket-placing groove.

A method of using a packing box comprises the following steps of:

opening the packing box, and turning over a cover of the packing box, after the cover of the packing box is turned over, the lower end of the cover and the lower end surface of the non-slip layer forms a bottom support surface, or after the cover is turned over, the lower end surface of the non-slip layer forms a bottom support surface;

placing the packing box after being turned over on a working surface with the cover being located under the box body, the bottom support surface being connected with the working surface, and the lower end surface of the non-slip layer being adhered or adsorbed to the working surface.

The method of using a packing box comprises the following step of:

locking the position determining protrusion of the box body in the position limiting slot of the support member, the box body being inclined and forming an angle with respect to the cover.

It should be noted that, the above-mentioned "first, second . . . " does not represent a specific number and order, but only are used for the distinction in names.

The advantages or principles of the present invention will be described below:

1. A packing box comprises a box body and a cover, the cover being connected on a swivel to box body; an inner side of the cover is provided with an non-slip layer, and the non-slip layer has a lower end surface having a corresponding non-slip setting; the lower end surface of the non-slip layer is flush with the lower end of the cover or protrudes with respect to the lower end of the cover; after the cover is turned over, the lower end of the cover and the lower end surface of the non-slip layer form a bottom support surface, or the lower end surface of the non-slip layer forms a bottom support surface; during use, the cover of the packing box is turned over, and after being turned over the packing box is placed on a working surface; the cover is located under the box body, and the bottom support surface is connected to the working surface; the lower end surface of the non-slip layer has a corresponding non-slip setting, which is connected with the working surface in a mode of slip-resistance and has a large friction coefficient. Therefore, during use, a great friction force exists between the non-slip layer and the working surface, and the packing box will not displace under a general force, thus having an non-slip effect.

The cover of the packing box has an non-slip setting, and the packing box has an anti-slip function, which makes it easy for people to use the packing box, can reduce the possibility of dropping, knocking over of the packing box and so on because of someone's carelessness, can protect the product in the packing box better to prevent it from dropping, losing or destroying, and facilitates the collection when not in use.

2. The lower end surface of the non-slip layer is adhered or adsorbed on a working surface; the packing box after being turned over is placed on the working surface and the non-slip layer can have a good non-slip effect.

3. An end of the cover and the box body is provided with a rotation block; a first rotation portion of the rotation block corresponds to the cover and is connected on a swivel to an end of the cover via a first rotation shaft in the first rotation portion, and a second rotation portion of the rotation block corresponds to the packing box and is connected on a swivel to an end of the box body via a second rotation shaft in the second rotation portion, thus, a connection being realized between the cover and the box body in a 360-degree swivel connection; the rotation block can be turned by 180 degrees, the swivel connection between the cover and the box body is simple, can realize a 360-degree swivel, makes it easier for people to use the packing box and achieves a better non-slip effect when the packing box is turned over.

4. The first shaft hole and the second shaft hole are respectively provided with an elastic member, and the elastic member allows the cover to hold at any turning angle; the elastic member in the first shaft hole is connected to the first rotation shaft, and the elastic member in the second shaft hole is connected to the second rotation shaft; the elastic member is a C-shaped elastic column as preferred; the elastic member may limit the location of the first rotation or second rotation shaft so that the cover can hold at any turning angle when it is turned over, which can make a better use of the packing box, for example, make it easy to clamp a bracket placed in the packing box.

5. The arrangement of the protruding portions and mounting recesses of the cover and box body can facilitate to realize a 360-degree swivel between the cover and box body via the rotation block; the rotation block is provided at two sides of the cover and the box body though the mounting recess, and it is properly arranged, evenly forced when rotating, and is hard to be destroyed; meanwhile, the arrangement of the protruding portions and mounting recesses makes the packing box more beautiful as a whole.

6. A side of the cover is provided with a fixing protrusion, a position limiting protrusion, and a support member; the fixing protrusion is distanced from the position limiting protrusion, the support member is provided with a rotation hole and a position limiting slot and is connected on a swivel to the fixing protrusion, and the position limiting slot fits the position limiting protrusion; a side of the box body is correspondingly provided with a position determining protrusion, and the position determining protrusion fits the position limiting protrusion; after the cover of the packing box is turned over, the position determining protrusion in the side of the box body is locked in the position limiting slot of the support member, and the box body is fixed and at an angle to the cover; the cover of the packing box after being turned over is placed on the working surface, and the box body is at an angle to the cover, which can facilitate to realize a specific function of some packing boxes; when the packing box is closed, the position limiting slot of the support member can fit the position limiting protrusion of the side of the cover, so that the support member is fixed.

7. The arrangement of the position determining slot on the support member can be used for changing the relative position of the box body and the cover and adjusting the angle between the box body and the cover.

8. The placing cavity of the box body of the packing box is provided with an inner holder provided with a plurality of bracket-placing grooves; the packing box is used for the package of the bracket, and has an non-slip setting; when the packing box is turned over and is placed on a working surface, the lower end surface of the non-slip layer is connected to the working surface in a mode of slip-resistance, which can effectively prevent the bracket packing box placed on the working surface from dropping, knocking over and so on because of carelessness and thus the bracket in the packing box drops and even loses when the doctor are proceeding with an orthodontia; the packing box protects the bracket better, prevents the doctor from lengthening their working hours or discontinuing their work due to the occurrence of the above condition, and effectively ensures the normal operation of the orthodontia by the doctor; a gap is left between the lower end surface of the non-slip layer and the upper surface of the inner holder, preventing the non-slip layer from adhering to the inner holder;

the packing box for packing the bracket is placed on the working surface, with the box body being at an angle and inclined with respect to the cover, and thus a bottom of the bracket will be inclined with respect to a horizontal plane; after the doctor clamps the bracket with a clamp, the bracket can be pasted on the tooth by a simple adjustment to facilitate the orthodontia by the doctor.

9. Different brackets correspond to different teeth positions, and the arrangement of the bracket placing mark can help the doctor to proceed with the orthodontia and clamp the corresponding bracket.

10. A boss is formed on the inner holder, and the plurality of bracket-placing grooves are provided on the boss; the arrangement of the boss can facilitate to clamp the bracket; the non-slip layer is provided with a through hole corresponding to the boss; the arrange of the through hole can prevent a surface of the boss and the bracket from adhering to the non-slip layer; the flange and the inner end portion of the cover form the placing groove; the non-slip layer is provided and locked in the placing groove of the cover.

11. The first bracket-placing grooves are regularly arranged along the first edge, the second bracket-placing grooves are regularly arranged along the second edge, and the first bracket-placing grooves correspond to the second bracket-placing grooves; the third bracket-placing grooves are regularly arranged between the first bracket-placing grooves and the second bracket-placing grooves; such an arrangement of bracket-placing grooves can facilitate the package of the bracket and the use of the bracket by the doctor in work.

12. The boss is in a shape of an ellipse, similar to the shape of human mouth when it is open; the first bracket-placing grooves are arranged in an arc along the first edge, and the second bracket-placing grooves are arranged in an arc along the second edge; this can facilitate to rapidly clamp corresponding bracket when the doctor proceeds with the orthodontia, bring convenience for the orthodontia by the doctor, and reduce the doctor's working time.

13. The number of the bracket-placing grooves is arranged corresponding to the arrangement of teeth of most people, which can be more beneficial to the package of the bracket and the use of the bracket by the doctor in work.

14. The bracket will be provided with the traction hooks in corresponding teeth positions, and the arrangement of the traction hook avoiding groove can have an avoidance effect on the bracket with traction hook, so as to facilitate the package and use of the bracket.

DESCRIPTION OF THE REFERENCE SIGNS

10 box body; 11 position determining protrusion; 12 inner holder; 121 boss; 13 bracket-placing groove; 131 first bracket-placing groove; 1311 traction hook avoiding groove; 132 second bracket-placing groove; 133 third bracket-placing groove; 20 cover; 21 non-slip layer; 211 through hole; 22 flange; 23 fixing protrusion; 231 locking convex; 24 position limiting protrusion; 25 support member; 251 rotation hole; 252 position limiting slot; 253 position determining slot; 30 rotation block; 31 first rotation portion; 32 second rotation portion; 33 first shaft hole; 34 second shaft hole; 35 first rotation shaft; 36 second rotation shaft; 37 elastic member; 41 protruding portion; 42 mounting recess.

DETAILED DESCRIPTION OF THE EMBODIMENTS

The following embodiments of the present disclosure are described in detail.

As shown in FIGS. 1-14, a packing box comprises a box body 10 and a cover 20, the cover 20 fits the box body 10, and an end of the cover 20 is connected on a swivel to an end of the box body 10; an inner side of the cover 20 is provided with an non-slip layer 21, and the non-slip layer 21 has a lower end surface being flush with a lower end of the cover 20 or protruding with respect to the lower end of the cover 20; after the cover 20 is turned over, the lower end of the cover 20 and the lower end surface of the non-slip layer 21 form a bottom support surface, or after the cover 20 is turned over, the lower end surface of the non-slip layer 21 forms a bottom support surface.

In this embodiment, the lower end surface of the non-slip layer 21 may be adhered or adsorbed on a working surface. In addition, the lower end surface of the non-slip layer 21 may be further provided with an non-slip protrusion or an non-slip texture.

Figure 12:
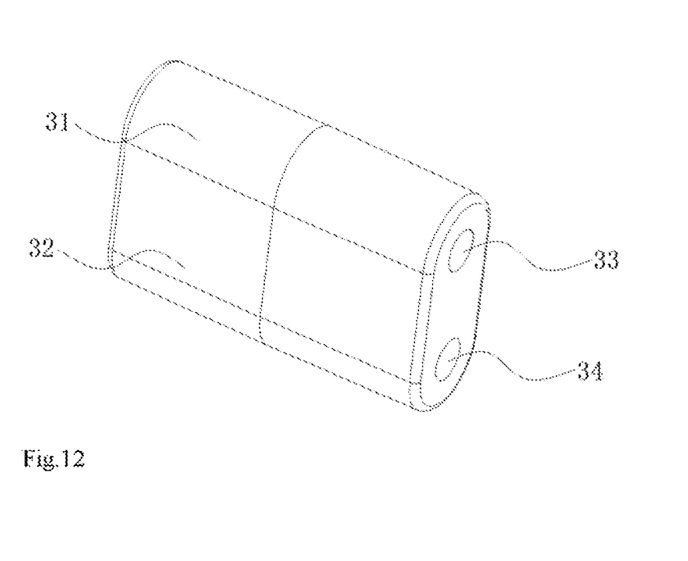
FIG. 12 is a schematic diagram of a steric structure of a rotation block according to an embodiment of the present disclosure.

Wherein, an end of the cover 20 and the box body 10 is provided with a rotation block 30, the rotation block 30 has a first rotation portion 31 and a second rotation portion 32 and is provided with at least two shaft holes; the shaft holes include at least a first shaft hole 33 provided in the first rotation portion 31 and a second shaft hole 34 provided in the second rotation portion 32; the first shaft hole 33 is provided with a first rotation shaft 35 connected to an end of the cover 20, and the second shaft hole 34 is provided with a second rotation shaft 36 connected to an end of the box body 10; the overturning angle of the cover 20 with respect to the box body 10 is 360 degrees.

Figure 13:
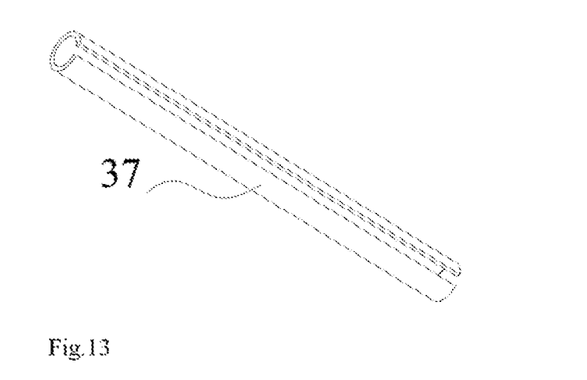
FIG. 13 is a schematic diagram of a steric structure of an elastic member according to an embodiment of the present disclosure.

The first shaft hole 33 and the second shaft hole 34 are respectively provided with an elastic member 37, and the elastic member 37 allows the cover 20 to hold at any turning angle; the elastic member 37 in the first shaft hole 33 is connected to the first rotation shaft 35, and the elastic member 37 in the second shaft hole 34 is connected to the second rotation shaft 36. In this embodiment, the elastic member 37 is a C-shaped elastic column.

Figure 1:
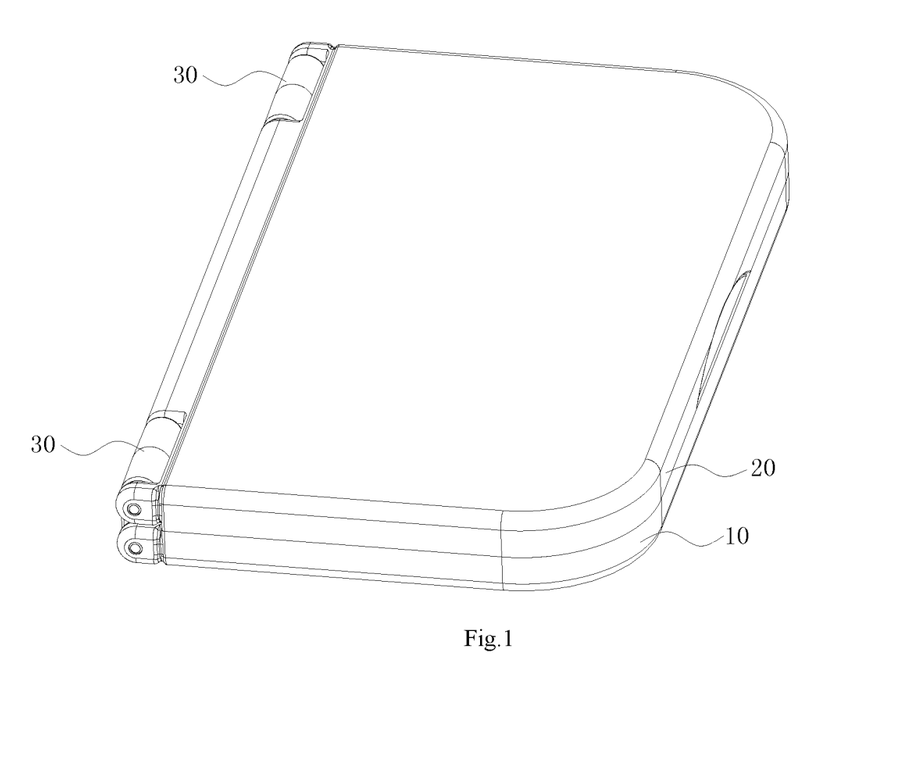
FIG. 1 is a schematic diagram of a steric structure of a packing box according to an embodiment of the present disclosure when it is closed.
Figure 2:
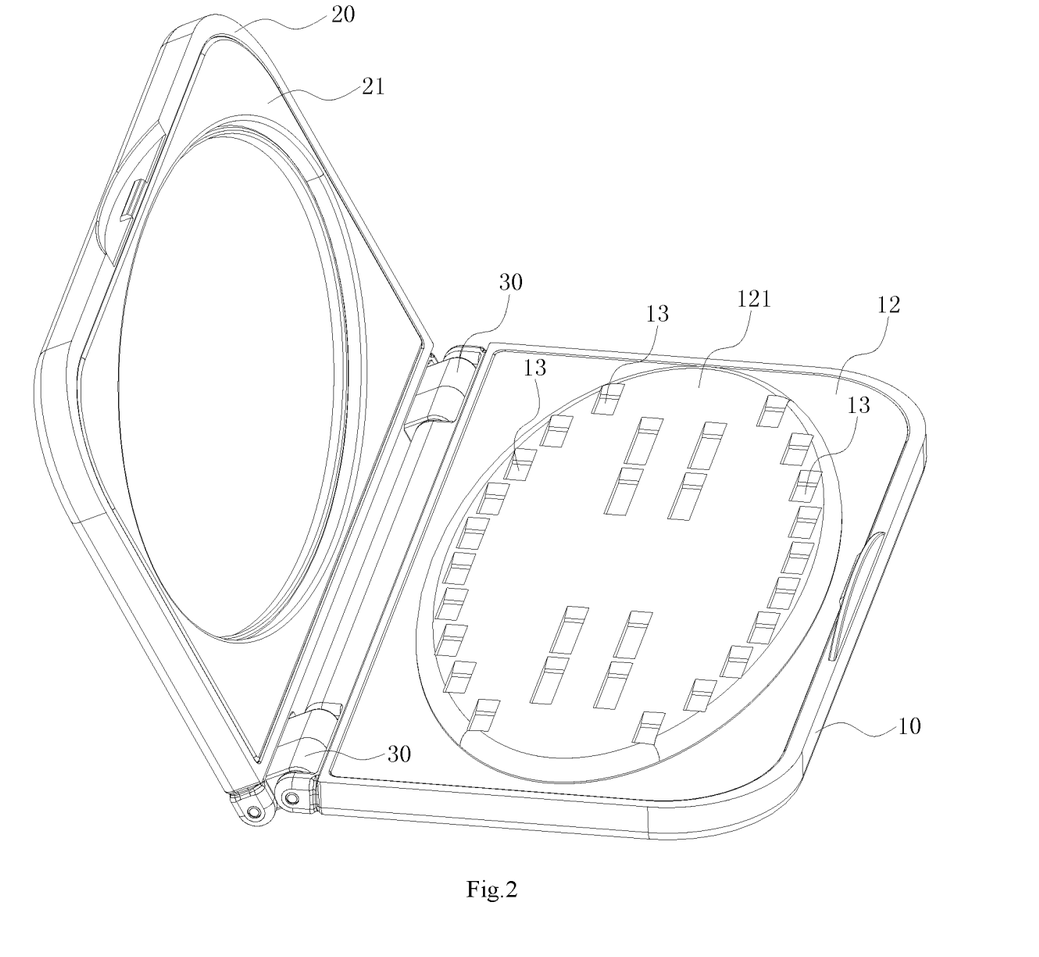
FIG. 2 is a schematic diagram of a steric structure of a packing box according to an embodiment of the present disclosure when it is open.
Figure 3:
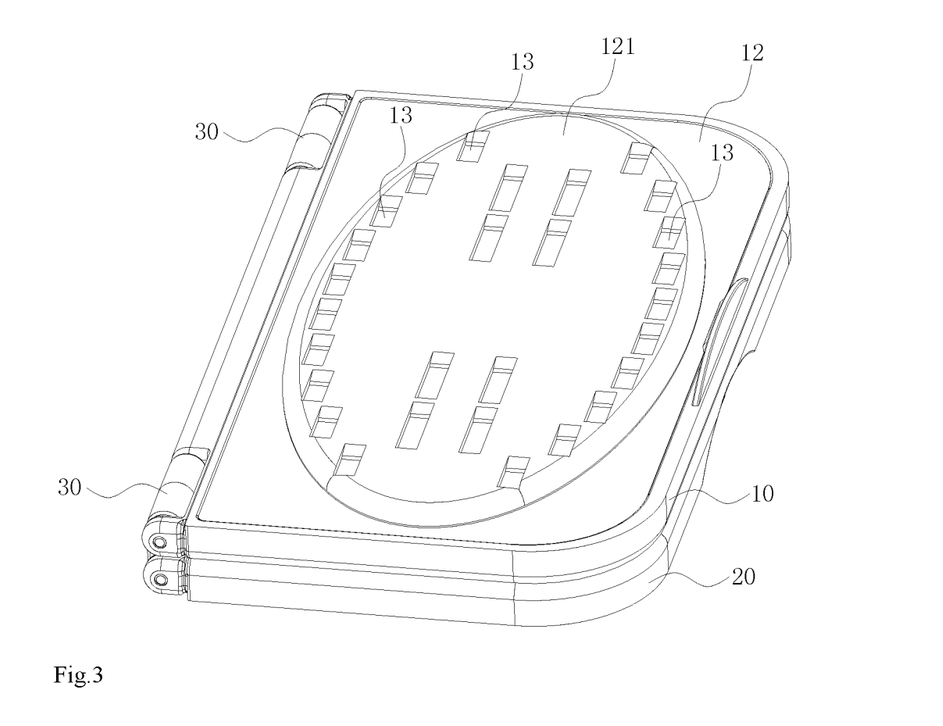
FIG. 3 is a schematic diagram of a steric structure of a packing box according to an embodiment of the present disclosure when it is turned over.
Figure 4:
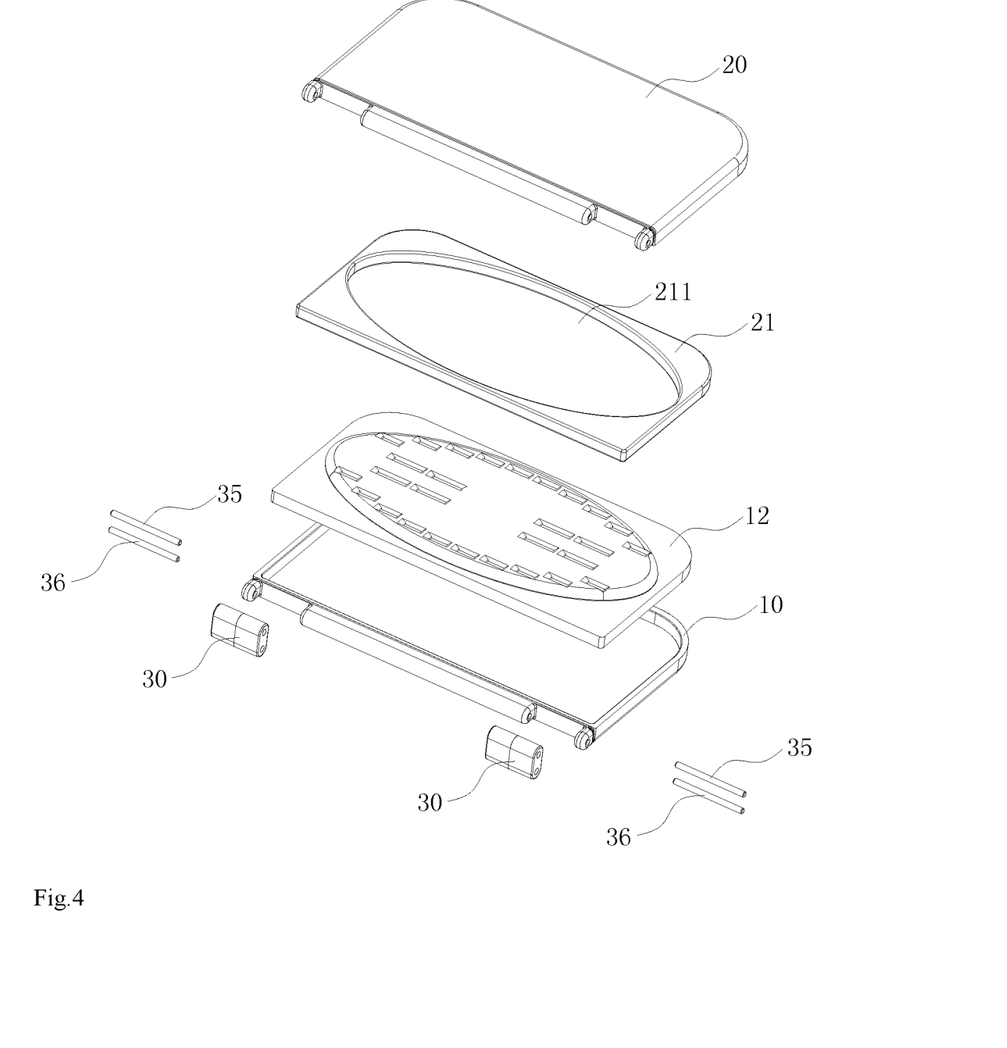
FIG. 4 is a schematic diagram of an exploded structure of a packing box according to an embodiment of the present disclosure.
Figure 5:
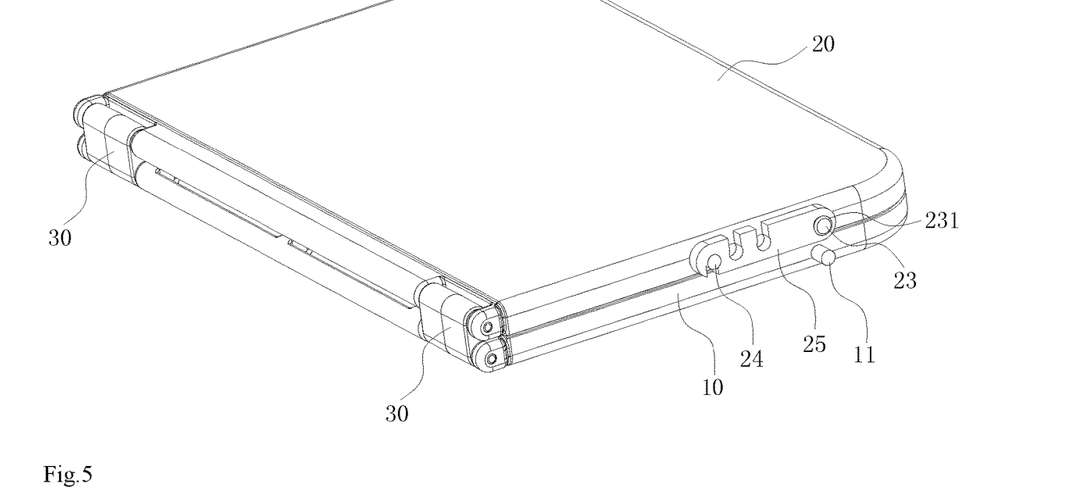
FIG. 5 is a schematic diagram of a steric structure of another packing box according to an embodiment of the present disclosure when it is closed.
Figure 6:
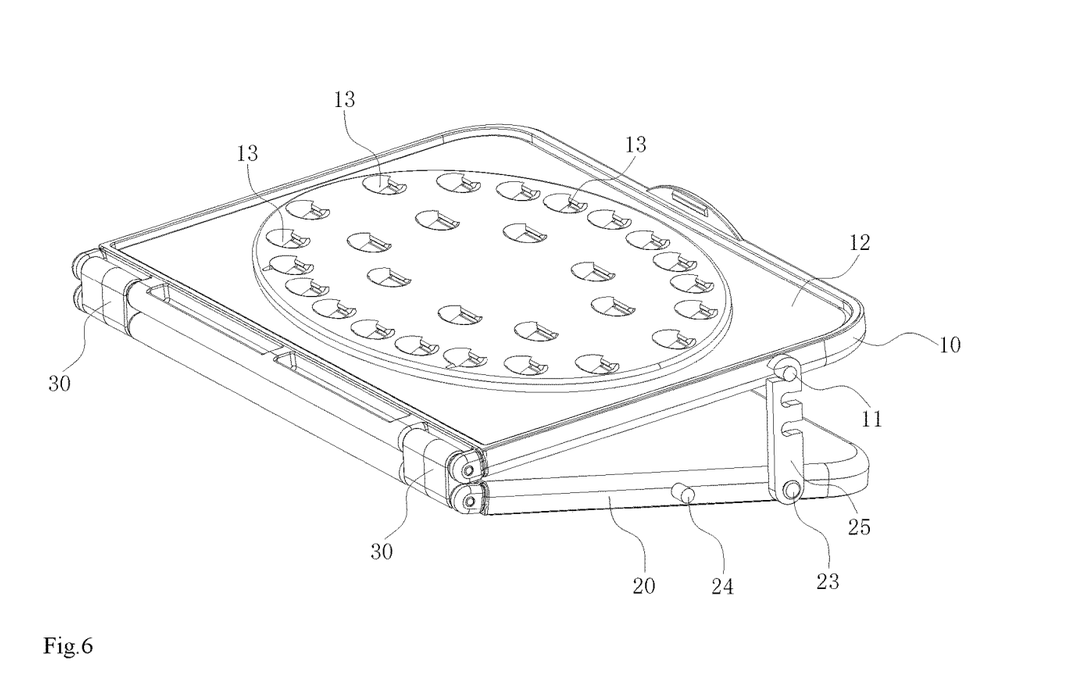
FIG. 6 is a schematic diagram of a steric structure of another packing box according to an embodiment of the present disclosure when it is turned over.
Figure 7:
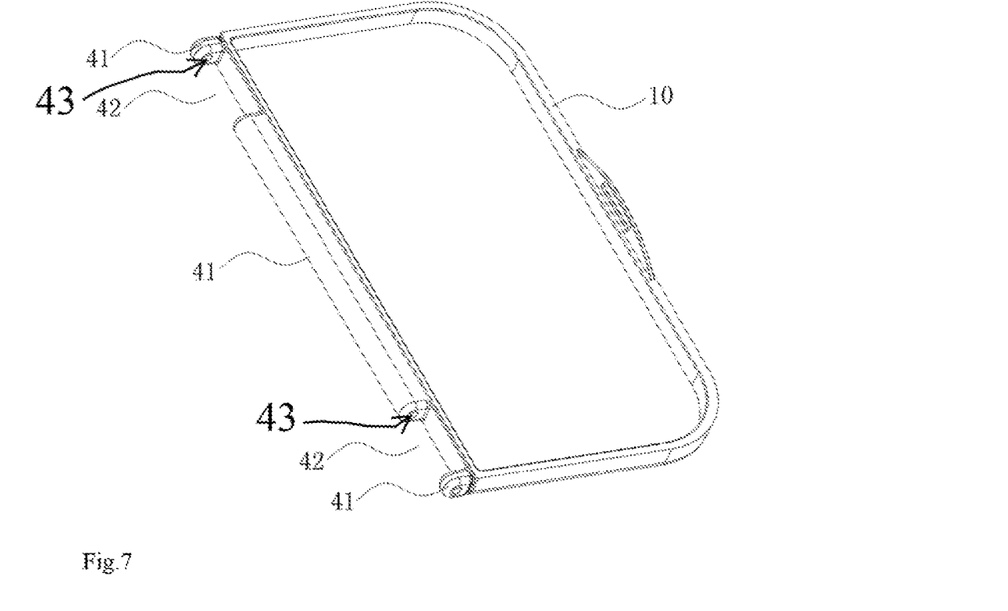
FIG. 7 is a schematic diagram of a steric structure of a box body according to an embodiment of the present disclosure.
Figure 8:
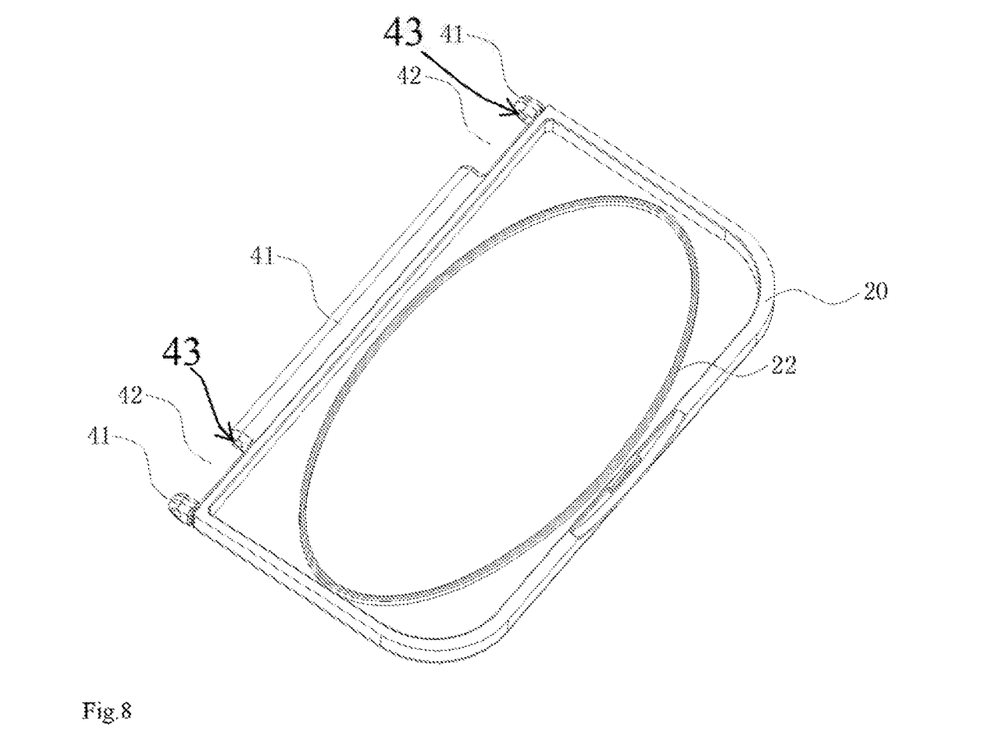
FIG. 8 is a schematic diagram of a steric structure of a cover according to an embodiment of the present disclosure.

An end of the cover 20 and box body 10 is respectively provided with a protruding portion 41, and the protruding portion 41 forms a mounting recess 42 on both sides of an end of the cover 20 and box body 10 respectively and is provided with a connection hole; the rotation block 30 is provided at the mounting recess 42 of the cover 20 and the box body 10, the first rotation shaft 35 is connected to the connection hole of the protruding portion 41 of the cover 20, and the second rotation shaft 36 is connected to the connecting hole of the protruding portion 41 of the box body 10.

Figure 14:
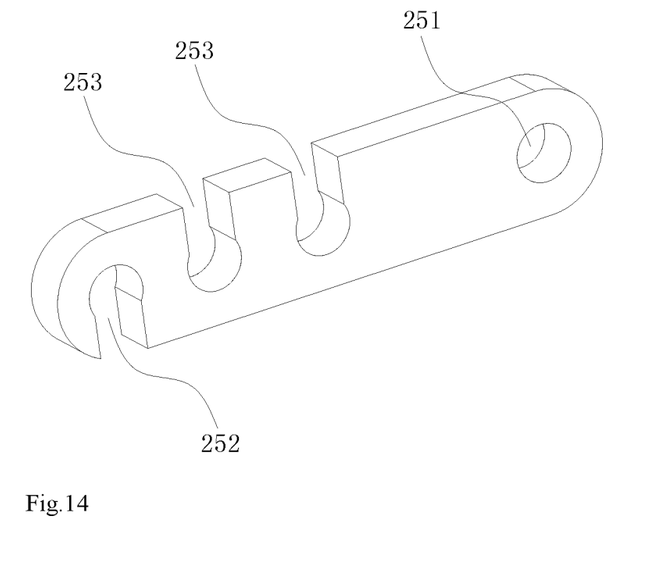
FIG. 14 is a schematic diagram of a steric structure of an support member according to an embodiment of the present disclosure.

In addition, at least one of two sides of the cover 20 is provided with a fixing protrusion 23, a position limiting protrusion 24, and a support member 25; the fixing protrusion 23 is distanced from the position limiting protrusion 24 and is provided with a locking convex 231 at an end, the support member 25 is provided with a rotation hole 251 and a position limiting slot 252 and is connected on a swivel to the fixing protrusion 23 though the rotation hole 251, and the position limiting slot 252 fits the position limiting protrusion 24; at least one of two sides of the box body 10 is provided with a position determining protrusion 11, and the position determining protrusion 11 corresponds to the position limiting protrusion 24 and fits the position limiting slot 252.

The support member 25 is further provided with a position determining slot 253; the position determining slot 253 fits the position determining protrusion 11, is provided between the rotation hole 251 and the position limiting slot 252 of the support member 25, and has an orientation that is the same as or opposite to the orientation of the position limiting slot 252.

Figure 9:
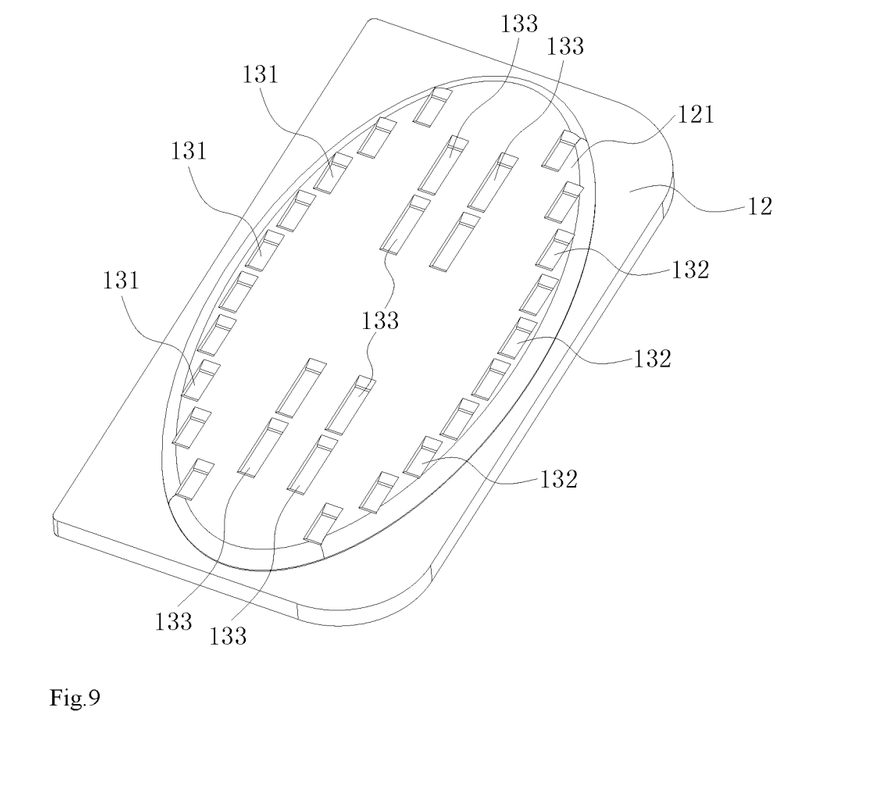
FIG. 9 is a schematic diagram of a steric structure of an inner holder according to an embodiment of the present disclosure.
Figure 10:
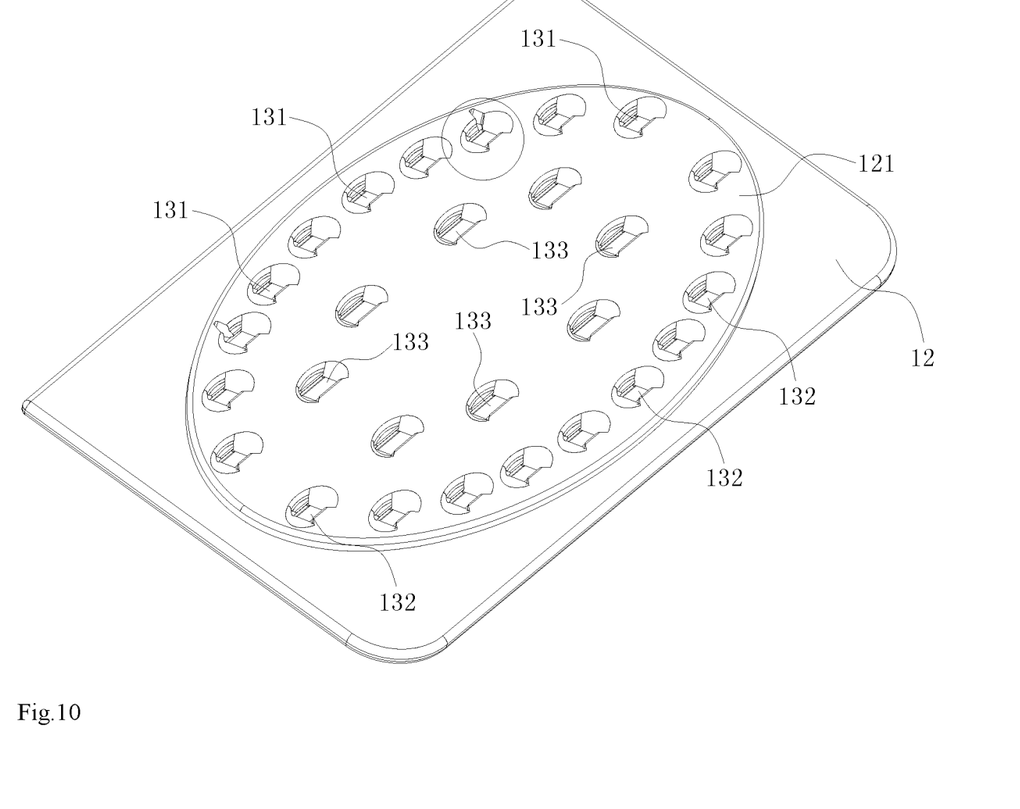
FIG. 10 is a schematic diagram of a steric structure of another inner holder according to an embodiment of the present disclosure.

The packing box further comprises an inner holder 12, and the box body 10 is provided with a placing cavity; the inner holder 12 is disposed in the placing cavity of the box body 10 and is provided with a plurality of bracket-placing grooves 13; the inner holder 12 has an upper surface, and a gap is left between the lower end surface of the non-slip layer 21 and the upper surface of the inner holder 12 when the packing box is closed.

The bracket-placing groove 13 has a placement mouth, a placement side portion and a placement bottom portion, and a corresponding placing mark is set on at least one of a surface of the inner holder 12 close to the placement mouth of the bracket-placing groove 13, the placement side portion of the bracket-placing groove 13 and the placement bottom portion of the bracket-placing groove 13.

the upper surface of the inner holder 12 is protruded upwardly to form a boss 121, and a plurality of bracket-placing grooves 13 are provided on the boss 121; the non-slip layer 21 is provided with a through hole 211 corresponding to the boss 121; the inner side of the cover 20 is provided with a flange 22 corresponding to the boss 121, and the flange 22 and an inner end portion of the cover 20 form the placing groove corresponding to the non-slip layer 21; the non-slip layer 21 is provided in the placing groove of the cover 20.

The boss 121 has a first edge and a second edge, and the bracket-placing grooves 13 are divided into first bracket-placing grooves 131, second bracket-placing grooves 132 and third bracket-placing grooves 133; the first bracket-placing grooves 131 are disposed adjacent to the first edge and regularly arranged along the first edge, the second bracket-placing grooves 132 are disposed adjacent to the second edge and regularly arranged along the second edge, and the first bracket-placing grooves 131 are corresponding to the second bracket-placing grooves 132; the third bracket-placing grooves 133 are regularly arranged between the first bracket-placing grooves 131 and the second bracket-placing grooves 132.

The boss 121 is in a shape of an ellipse, the first bracket-placing grooves 131 are disposed adjacent to the first edge and arranged in an arc along the first edge, and the second bracket-placing grooves 132 are disposed adjacent to the second edge and arranged in an arc along the second edge.

Figure 11:
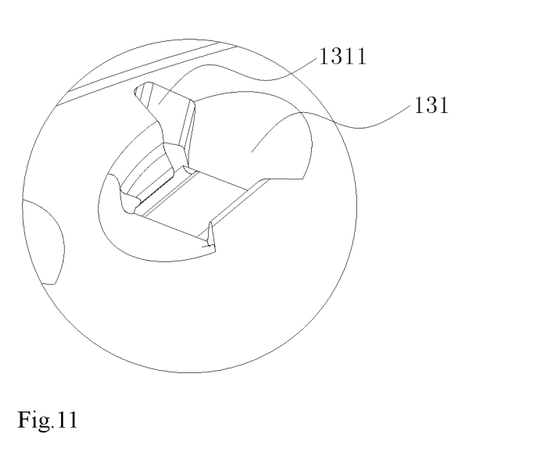
FIG. 11 is a partially enlarged view of FIG. 10.

There are twenty-eight bracket-placing grooves 13, consisting of ten first bracket-placing grooves 131, ten second bracket-placing grooves 132 and eight third bracket-placing grooves 133. Among the ten first bracket-placing grooves 131 regularly arranged, the third of the first bracket-placing grooves 131 and the eighth of the first bracket-placing grooves 131 are respectively provided with a traction hook avoiding groove 1311; the traction hook avoiding groove 1311 is communicated with the first bracket-placing groove 131 and protrudes outwardly with respect to the first bracket-placing groove 131.

A method of using a packing box, wherein it comprises the following steps of:

opening the packing box, and turning over a cover 20 of the packing box, after the cover 20 of the packing box is turned over, the lower end of the cover 20 and the lower end surface of the non-slip layer 21 form a bottom support surface, or after the cover 20 is turned over, the lower end surface of the non-slip layer 21 forms a bottom support surface;

Placing the packing box with the cover thereof being turned over on a working surface, wherein the cover 20 is located under the box body 10, the bottom support surface is connected with the working surface, and the lower end surface of the non-slip layer 21 is adhered or adsorbed to the working surface.

The method of using a packing box further comprises the following step of:

locking the position determining protrusion 11 of the box body 10 in the position limiting slot 252 of the support member 25, the box body 10 being inclined and forming an angle with respect to the cover 20.

The advantages of the present embodiment, 1. a packing box comprises a box body 10 and a cover 20, the cover 20 being connected on a swivel to box body; an inner side of the cover 20 is provided with an non-slip layer 21, and the non-slip layer 21 has a lower end surface having a corresponding non-slip setting; the lower end surface of the non-slip layer 21 is flush with a lower end of the cover 20 or protrudes with respect to the lower end of the cover 20; after the cover 20 is turned over, the cover 20 and the lower end of the non-slip layer 21 form a bottom support surface, or the lower end surface of the non-slip layer 21 forms a bottom support surface; during use, the cover of the packing box 20 is turned over, and after being turned over, the packing box is placed on a working surface; the cover 20 is located under the box body 10, and the bottom support surface is connected to the working surface; the lower end surface of the non-slip layer 21 has a corresponding non-slip setting, which is connected with the working surface in a mode of slip-resistance and has a large friction coefficient. Therefore, during use, a great friction force exists between the non-slip layer and the working surface, and the packing box will not displace under a general force, thus having an non-slip effect.

The cover 20 of the packing box has an non-slip setting, and the packing box has an anti-slip function, which makes it easy for people to use the packing box, can reduce the possibility of dropping, knocking over of the packing box and so on because of someone's carelessness, can protect the product in the packing box better to prevent it from dropping, losing or destroying, and facilitates the collection when not in use.

2. The lower end surface of the non-slip layer 21 is adhered or adsorbed on a working surface; the packing box after being turned over is placed on the working surface and the non-slip layer 21 can have a good non-slip effect.

3. An end of the cover 20 and the box body 10 is provided with a rotation block 30; a first rotation portion 31 of the rotation block 30 corresponds to the cover 20 and is connected on a swivel to an end of the cover 20 via a first rotation shaft 35 in the first rotation portion 31, and a second rotation portion 32 of the rotation block 30 corresponds to the packing box 10 and is connected on a swivel to an end of the box body 10 via a second rotation shaft 36 in the second rotation portion 32, thus, a 360-degree swivel connection being realized between the cover 20 and the box body 10; the rotation block 30 can be turned by 180 degrees, the swivel connection between the cover 20 and the box body 10 is simple, can realize a 360-degree swivel, makes it easier for people to use the packing box and achieves a better non-slip effect when the packing box is turned over.

4. The first shaft hole 33 and the second shaft hole 34 are respectively provided with an elastic member 37, and the elastic member 37 allows the cover 20 to hold at any turning angle; the elastic member 37 in the first shaft hole 33 is connected to the first rotation shaft, and the elastic member 37 in the second shaft hole 34 is connected to the second rotation shaft 36; the elastic member 37 is a C-shaped elastic column as preferred; the elastic member may limit the location of the first rotation 35 or second rotation shaft 36 so that the cover 20 can hold at any turning angle when it is turned over, which can make a better use of the packing box, for example, make it easy to clamp a bracket placed in the packing box.

5. The arrangement of the protruding portions 41 and mounting recesses 42 of the cover 20 and box body 10 can facilitate to realize a 360-degree swivel between the cover 20 and box body 10 via the rotation block 30; the rotation block 30 is provided at two sides of the cover 20 and the box body 10 though the mounting recess 42, and it is properly arranged, evenly forced when rotating, and is hard to be destroyed; meanwhile, the arrangement of the protruding portions 41 and mounting recesses 42 makes the packing box more beautiful as a whole.

6. A side of the cover 20 is provided with a fixing protrusion 23, a position limiting protrusion 24, and a support member 25; the fixing protrusion 23 is distanced from the position limiting protrusion 24, the support member 25 is provided with a rotation hole 251 and a position limiting slot 252 and is connected on a swivel to the fixing protrusion 23, and the position limiting slot 252 fits the position limiting protrusion 24; a side of the box body 10 is correspondingly provided with a position determining protrusion 11, and the position determining protrusion 11 fits the position limiting protrusion 24; after the cover 20 of the packing box is turned over, the position determining protrusion 11 in the side of the box body 10 is locked in the position limiting slot 252 of the support member 25, and the box body 10 is fixed and at an angle to the cover 20; the cover 20 of the packing box after being turned over is placed on the working surface, and the box body 10 is at an angle to the cover 20, which can facilitate to realize a specific function of some packing boxes; when the packing box is closed, the position limiting slot 252 of the support member 25 can fit the position limiting protrusion 24 of the side of the cover 20, so that the support member 25 is fixed.

7. The arrangement of the position determining slot 253 on the support member 25 can be used for changing the relative position of the box body 10 and the cover 20 and adjusting the angle between the box body 10 and the cover 20.

8. The placing cavity of the box body 10 of the packing box is provided with an inner holder 12 provided with a plurality of bracket-placing grooves 13; the packing box is used for the package of the bracket, and has an non-slip setting; when the packing box is turned over and is placed on a working surface, the lower end surface of the non-slip layer 21 is connected to the working surface in a mode of slip-resistance, which can effectively prevent the bracket packing box placed on the working surface from dropping, knocking over and so on because of carelessness and thus the bracket in the packing box drops and even loses when the doctor are proceeding with an orthodontia; the packing box protects the bracket better, prevents the doctor from lengthening their working hours or discontinuing their work due to the occurrence of the above condition, and effectively ensures the normal operation of the orthodontia by the doctor; a gap is left between the lower end surface of the non-slip layer 21 and the upper surface of the inner holder 12, preventing the non-slip layer 21 from adhering to the inner holder 12.

The packing box for packing the bracket is placed on the working surface, with the box body 10 being at an angle and inclined with respect to the cover 20, and thus a bottom of the bracket will be inclined with respect to a horizontal plane; after the doctor clamps the bracket with a clamp, the bracket can be pasted on the tooth by a simple adjustment to facilitate the orthodontia by the doctor.

9. Different brackets correspond to different teeth positions, and the arrangement of the bracket placing mark can help the doctor to proceed with the orthodontia and clamp the corresponding bracket.

10. A boss 121 is formed on the inner holder 12, and the plurality of bracket-placing grooves 13 are provided on the boss 121; the arrangement of the boss 121 can facilitate to clamp the bracket; the non-slip layer 21 is provided with a through hole 211 corresponding to the boss 121; the arrange of the through hole 211 can prevent a surface of the boss 121 and the bracket from adhering to the non-slip layer 21; the flange 22 and the inner end portion of the cover 20 form the placing groove; the non-slip layer 21 is provided and locked in the placing groove of the cover 20.

11. The first bracket-placing grooves 131 are regularly arranged along the first edge, the second bracket-placing grooves 132 are regularly arranged along the second edge, and the first bracket-placing grooves 131 correspond to the second bracket-placing grooves 132; the third bracket-placing grooves 133 are regularly arranged between the first bracket-placing grooves 131 and the second bracket-placing grooves 132; such an arrangement of bracket-placing grooves 13 can facilitate the package of the bracket and the use of the bracket by the doctor in work.

12. The boss 121 is in a shape of an ellipse, similar to the shape of human mouth when it is open; the first bracket-placing grooves 131 are arranged in an arc along the first edge, and the second bracket-placing grooves 132 are arranged in an arc along the second edge; this can facilitate to rapidly clamp corresponding bracket when the doctor proceeds with the orthodontia, bring convenience for the orthodontia by the doctor, and reduce the doctor's working time.

The number of the bracket-placing grooves 13 is arranged corresponding to the arrangement of teeth of most people, which can be more beneficial to the package of the bracket and the use of the bracket by the doctor in work.

The bracket will be provided with the traction hooks in corresponding teeth positions, and the arrangement of the traction hook avoiding groove 1311 can have an avoidance effect on the bracket with traction hook, so as to facilitate the package and use of the bracket.

The above are only specific embodiments of the present disclosure and is not intended to limit the scope of the present disclosure; Any substitution or improvement made without departing from its spirit of the present disclosure should fall into the protection scope of the present disclosure.

The invention claimed is:

1. A packing box, comprising a box body and a cover, wherein the box body and cover have matching shapes;
    an end of the cover is rotatably connected to an end of the box body;
    an inside surface of the cover is provided with a non-slip layer; wherein
    the non-slip layer has a bottommost surface that protrudes above a peripheral surface of the cover inside surface; such that the inside surface of the cover comprising the non-slip forms a bottom support surface for the packing box when the cover is turned over; and
    the box body comprises an inner holder disposed within a placing cavity; wherein the inner holder is provided with a plurality of bracket-placing groove.

2. The packing box according to claim 1, wherein the non-slip layer provides frictional contact with on a working surface.

3. The packing box according to claim 1, wherein a rotation block is provided at an end of the cover and an end of the box body, the rotation block has a first rotation portion and a second rotation portion and is provided with at least two shaft holes; the shaft holes include at least a first shaft hole provided in the first rotation portion and a second shaft hole provided in the second rotation portion; the first shaft hole is provided with a first rotation shaft connected to the end of the cover, and the second shaft hole is provided with a second rotation shaft connected to the end of the box body; the cover is rotatably connected to the box body so as to allow a 360 degree rotational movement.

4. The packing box according to claim 3, wherein each of the first shaft hole and the second shaft hole is provided with an elastic member therein, and the elastic member allows the cover to stay at any turning angle; the elastic member in the first shaft hole is connected to the first rotation shaft, and the elastic member in the second shaft hole is connected to the second rotation shaft.

5. The packing box according to claim 4, wherein the elastic member is a C-shaped elastic column.

6. The packing box according to claim 3, wherein each of the end of the cover and the end of box body is provided with a protruding portion, the protruding portion forms mounting recesses on both sides of the end of the cover or the end of the box body respectively, and the protruding portion is provided with a connection hole; wherein the rotation block is positioned at the mounting recesses of the cover and the box body, the first rotation shaft is connected to the connection hole of the protruding portion of the cover, and the second rotation shaft is connected to the connecting hole of the protruding portion of the box body.

7. The packing box according to claim 1, wherein the packing the inner holder has an upper surface that is spaced from the non-slip layer of the cover when packing box is closed.

8. The packing box according to claim 7, wherein the bracket-placing groove has a placement mouth, a placement side portion and a placement bottom portion.

9. The packing box according to claim 7, wherein the upper surface of the inner holder is protruded upwardly to form a boss, and the plurality of bracket-placing grooves are disposed on the boss; the non-slip layer is provided with a through hole corresponding to the boss; and the inner side of the cover is provided with a flange corresponding to the boss, the flange and an inner end portion of the cover form the placing groove corresponding to the non-slip layer; the non-slip layer is disposed in the placing groove of the cover.

10. The packing box according to claim 9, wherein the boss has a first edge and a second edge, and the bracket-placing grooves are divided into first bracket-placing grooves, second bracket-placing grooves and third bracket-placing grooves; the first bracket-placing grooves are disposed adjacent to the first edge and regularly arranged along the first edge, the second bracket-placing grooves are disposed. adjacent to the second edge and regularly arranged along the second edge, and the first bracket-placing grooves are corresponding to the second bracket-placing grooves; the third bracket-placing grooves are regularly arranged between the first bracket-placing grooves and the second bracket-placing grooves.

11. The packing box according to claim 10, wherein the boss is ellipse shaped, the first bracket-placing grooves are disposed adjacent to the first edge and arranged in an arc along the first edge, and the second bracket-placing grooves are disposed adjacent to the second edge and arranged in an arc along the second edge.

12. The packing box according to claim 10, wherein there are twenty-eight bracket-placing grooves, consisting of ten first bracket-placing grooves, ten second bracket-placing grooves and eight third bracket-placing grooves.

13. The packing box according to claim 12, wherein among the ten first bracket-placing grooves regularly arranged, the third one of the first bracket- placing grooves and the eighth one of the first bracket-placing grooves each is provided with a traction hook avoiding groove; the traction hook avoiding groove is communicated with the first bracket-placing groove and protrudes outwardly with respect to the first bracket-placing groove.

14. A packing box, comprising a box body and a cover, wherein the box body and cover have matching shapes; and
an end of the cover is rotatably connected to an end of the box body; and
an inside surface of the cover is provided with an non-slip layer; wherein
the non-slip layer has a bottommost surface that is level with a peripheral surface of the cover inside surface; such that the inside surface of the cover comprising the non-slip surface forms a bottom support surface for the packing box when the cover is turned over; and
the cover also comprises:
a fixing protrusion,
a position limiting protrusion, and
a support member; wherein
the fixing protrusion is distanced from the position limiting protrusion, the fixing protrusion includes a convex locking area at one end; wherein
the support member has a rotation hole and a position limiting slot and is connected on a swivel to the fixing protrusion though the rotation hole, and the position limiting slot accepts the position limiting protrusion; and
at least one of two sides of the box body is provided with a position determining protrusion, and the position determining protrusion corresponds to the position limiting protrusion and fits the position-limiting slot.

15. The packing box according to claim 14, wherein the support member is further provided with a position determining slot; the position determining slot fits the position determining protrusion, is provided between the rotation hole and the position limiting slot of the support member, and has an orientation being the same as or opposite to that of the position limiting slot.

* * * * *